United States Patent [19]
Ibáñez et al.

[11] Patent Number: 5,789,565
[45] Date of Patent: Aug. 4, 1998

[54] SERINE THREONINE KINASE RECEPTOR, ALK-7

[75] Inventors: Carlos F. Ibáñez, Västmannagatan 95, 113 43 Stockholm; Mikael Rydén, Hägersten; Henrik Jörnvall, Sundbyberg, all of Sweden

[73] Assignee: Carlos F. Ibanez, Stockholm, Sweden

[21] Appl. No.: 805,166

[22] Filed: Feb. 24, 1997

Related U.S. Application Data

[60] Division of Ser. No. 341,916, Nov. 15, 1994, Pat. No. 5,614,609, which is a continuation-in-part of Ser. No. 325, 956, Oct. 20, 1994, abandoned.

[51] Int. Cl.$^6$ .......................... C07H 21/04; C12N 15/12; C12N 15/63; C12N 15/85
[52] U.S. Cl. ...................... 536/23.5; 435/320.1; 435/325
[58] Field of Search .................... 536/23.5; 435/320.1, 435/325

[56] References Cited

FOREIGN PATENT DOCUMENTS

| | | |
|---|---|---|
| 0 171 496 | 2/1986 | European Pat. Off. . |
| 0 173 494 | 3/1986 | European Pat. Off. . |
| 0 184 187 | 6/1986 | European Pat. Off. . |
| WO 86/01533 | 3/1986 | WIPO . |
| WO 90/09441 | 8/1990 | WIPO . |
| WO 93/03743 | 3/1993 | WIPO . |
| WO 94/11502 | 5/1994 | WIPO . |
| WO 95/07928 | 3/1995 | WIPO . |

OTHER PUBLICATIONS

Attisano, L. et al., "Identification of Human Activin and TGFβ Type I Receptors That Form Heteromeric Kinase Complexes with Type II Receptors," *Cell* 75:671–680 (1993).
Beidler, C.B. et al., "Cloning and High Level Expression of a Chimeric Antibody with Specificity for Human Carcinoembryonic Antigen," *J. Immunol.* 141:4053–4060 (1988).
Benoist, C. and Chambon, P., "In vivo sequence requirements of the SV40 early promoter region," *Nature* 290:304–310 (1981).
Better, M. et al., "*Escherichia coli* Secretion of an Active Chimeric Antibody Fragment," *Science* 240:1041–1043 (1988).
Bollon, A.P. and Stauver, M., "DNA Transformation Efficiency of Various Bacteria and Yeast–Host Vector Systems," *J. Clin. Hematol. Oncol.* 10:39–48 (1980).
Botstein, D. et al., "Making mutations in vitro and putting them back into yeast," *Miami Winter Symposium* 19:265–274 (1982).
Breakefield, X.O. and DeLuca, N.A., "Herpes Simplex Virus for Gene Delivery to Neurons," *The New Biologist* 3(3):203–218 (1991).
Broach, J.R., "The Yeast Plasmid 2μ Circle," in: *The Molecular Biology of the Yeast Saccharomyces: Life Cycle and Inheritance*, Cold Spring Harbor Laboratory Press, Cold Spring Harbor, NY, pp. 445–470 (1981).
Broach, J.R., "the Yeast Plasmid 2μ Circle," *Cell* 28:203–204 (1982).
Cenatiempo, Y., "Prokaryotic gene expression in vitro: transcription–translation coupled systems," *Biochimie* 68:505–515 (1986).
Chater, K.F. et al., "*Streptomyces* øC31–like Phages: Cloning Vectors, Genome Changes and Host Range," *Sixth International Symposium on Actinomycetes Biology*, Kaido, Budapest, Hungary, pp. 45–54 (1985).
Cull, M.C. et al., Sreening for receptor ligands using large libraries of peptides linked to the C terminus of the *lac* repressor, *Proc. Natl. Acad. Sci. USA* 89:1865–1869 (1992).
Ebner, R. et al., "Cloning of a Type I TGF–β Receptor and Its Effect on TGF–β Binding to the Type II Receptor, "*Science* 260:1344–1348 (1993).
Flannigan, J.G. and Leder, P., "The *kit* Ligand: A Cell Surface Molecule Altered in Steel Mutant Fibroblasts,"*Cell* 63:185–194 (1990).
Franzén, P. et al., "Cloning of a TGFβ Type I Receptor That forms a Heteromeric Complex with the TGFβ Type II Receptor," *Cell* 75:681–692 (1993).
Gazit, A. et al., "Expression of the Normal Human *sis* /PDGF–2 Coding Sequence Induces Cellular Transformation," *Cell* 39:89–97 (1984).
Gilman, M.Z. et al., "Isolation of sigma–28–specific promoters from *Bacillus subtilis* DNA," *Gene* 32:11–20 (1984).
Glick, B.R. and Whitney, G.K., "Factors affecting the expression of foreign proteins in *Eschericia coli* ," *J. Ind. Microbiol.* 1:277–282 (1987).
Goding, J.W., "Conjugation of Antibodies with Fluorochromes: Modifications to the Standard Methods," *J. Immunol. Meth.* 13:215–226 (1976).
Gold, L. et al., "Translation Initiation in Prokaryotes," *Ann. Rev. Microbiol.* 35:365–403 (1981).
Gottesman, S., "Bacterial Regulation: Global Regulatory Networks," *Ann. Rev. Genet.* 18:415–441 (1984).

(List continued on next page.)

*Primary Examiner*—Paula K. Hutzell
*Assistant Examiner*—Stephen Gucker
*Attorney, Agent, or Firm*—Sterne, Kessler, Goldstein & Fox, P.L.L.C.

[57] ABSTRACT

The present invention relates, in general, to a novel serine threonine kinase receptor, ALK-7. In particular, the present invention relates to nucleic acid molecules coding for ALK-7; ALK-7 polypeptides; recombinant nucleic acid molecules; cells containing the recombinant nucleic acid molecules; antibodies having binding affinity specifically to ALK-7; hybridomas containing the antibodies; nucleic acid probes for the detection of ALK-7 nucleic acid; a method of detecting ALK-7 nucleic acid or polypeptide in a sample; and kits containing nucleic acid probes or antibodies. This invention further relates to bioassays using the nucleic acid sequence, receptor protein or antibodies of this invention to diagnose, assess, or prognose a mammal afflicted with neurodegenerative disease. Therapeutic uses for ALK-7 are also provided. This invention also relates to ligands, agonists, and antagonists of the ALK-7 receptor, and diagnostic and therapeutic uses thereof.

5 Claims, No Drawings

OTHER PUBLICATIONS

Gritz, L. and Davies, J., "Plasmid–encoded hygromycin B resistance: the sequence of hygromycin B phosphotransferase gene and its expression in *Escherichia coli* and *Saccharomyces cerevisiae*,"*Gene* 25:179–188 (1983).

Gryczan, T.J., "Molecular Cloning in *Bacillus subtilis*," in: *The Molecular Biology of the Bacilli*, Academic Press, NY, pp. 307–329 (1982).

Hamer, D. and Walling, M.J., "Regulation In vivo of a Cloned Mammalian Gene: Cadmium Induces the Transcription of a Mouse Metallothionein Gene in SV40 Vectors," *J. Mol. Appl. Gen.* 1:273–288 (1982).

He, W.W. et al., "Developmental Expression of Four Novel Serine/Threonine Kinase Receptors Homologous to the Activin/Transforming Growth Factor–β Type II Receptor Family," *Develop. Dynamics* 196:133–142 (1993).

Huang, Q. et al., "Introduction of a Foreign Gene(*Escherichia coli*lacZ) into Rat Neostriatal Neurons Using Herpes Simplex Virus Mutants: A Light and Electron Microscopic Study,"*Experimental Neurology* 115:303–316 (1992).

Jasny, B.R., "Insect Viruses Invade Biotechnology," *Science* 238:1653 (1987).

John, J.F. and Twitty, J.A., "Plasmids as Epidemiologic Markers in Nosocomial Gram–Negative Bacilli: Experience at a University and Review of the Literature," *Rev. Infect. Dis.* 8(5):693–704 (1986).

Johnson, S.A. and Hopper, J.E. "Isolation of the yeast regulatory gene GAL4 and analysis of its dosage effects on the galactose/melibiose regulon," *Proc. Natl. Acad. Sci. USA* 79:6971–6975 (1982).

Jones, P.T. et al., "Replacing the complimentarity–determining regions in a human antibody with those from a mouse," *Nature* 321:522–525 (1986).

Kendall, K.J. and Cohen, S.N., "Plasmid Transfer in *Streptomyces lividans*: Identification of a kil–kor System Associated with the transfer region of pIJ101," *J. Bacteriol.* 169(9):4177–4183 (1987).

Klein, R. et al., "the trkB Tyrosine Protein Kinase Is a Receptor for Brain–Derived Neurotrophic Factor and Neurotrophin–3," *Cell* 66:395–403 (1991).

Lam, K.S. et al., "A new type of synthetic peptide library for identifying ligand–binding activity," *Nature* 354:82–84 (1991).

Lindvall, O. et al., "Human fetal Dopamine Neurons Grafted Into the Striatum in Two Patients with Severe Parkinson's Disease: A Detailed Account of Methodology and a 6–month Follow–up," *Arch. Neurol.* 46:615–631 (1989).

Liu, A.Y. et al., "Production of a Mouse–Human Chimeric Monoclonal Antibody to CD20 with Potent Fc–Dependent Biologic Activity," *J. Immunol.* 139(10):3521–3526 (1987).

Liu, A.Y. et al., "Chimeric mouse–human IgG1 antibody that can mediate lysis of cancer cells," *Proc. Natl. Acad. Sci. USA* 84:3439–3443 (1987).

Matsuzaki, K. et al., "A Widely Expressed Transmembrane Serine/Threonine Kinase That Does Not Bind Activin, Inhibin, Transforming Growth Factor β, or Bone Morphogenic Factor,"*J. Biol. Chem.* 268(17): 12719–12723 (1993).

McKnight, S.L., "Functional Relationships between Transciptional Control Signals of the Thymidine Kinase Gene of Herpes Simplex Virus," *Cell* 31:355–365 (1982).

Metcalf, D., "The Molecular Biology and Functions of the Granulocyte–Macrophage Colony Stimulating Factors," *Blood* 67(2):257–267 (1986).

Miki, T. et al., "An efficient directional cloning system to construct cDNA libraries containing full–length insert at high–frequency," *Gene* 83:137–146 (1989).

Miki, T. et al., "Expression cDNA Cloning of the KGF Receptor by Creation of a Transforming Autocrine Loop," *Science* 251:72–75 (1991).

Miller, D.W. et al., "An Insect Baculovirus Host–Vector System for High–Level Expression of Foreign Genes," in: *Genetic Engineering, vol. 8*, Setlow, J.K., et al., eds., Plenum Press, pp. 277–297 (1986).

Morrison, S.L., "Transfectomas Provide Novel Chimeric Antibodies," *Science* 229:1202–1207 (1985).

Mulligan, R.C., "The Basic Science of Gene Therapy," *Science* 260:926–932 (1993).

Nishimura, Y. et al., "Recombinant Human–Mouse Chimeric Monoclonal Antibody Specific for Common Acute Lymphocytic Leukemia Antigen," *Cancer Res.* 47:999–1005 (1987).

Oi, V.T. and Morrison, S.L., "Chimeric Antibodies," *BioTechniques* 4(3):214–221 (1986).

Okayama, H. and Berg, P., "A cDNA Cloning Vector That Permits Expression of cDNA Inserts in Mammalian Cells," *Molec. Cell. Biol.* 3(2):280–289 (1983).

Riedel, H. et al., "Cytoplasmic domains determine signal specificity, cellular routing characteristics and influence ligand binding of epidermal growth factor and insulin receptors," *EMBO J.* 8(10):2943–2954 (1989).

Reidel, H. et al., "A chimaeric receptor allows insulin to stimulate tyrosine kinase activity of epidermal growth factor receptor," *Nature* 324:68–70 (1986).

Rubin, G.M., "*Drosophila melanogaster* as an Experimental Organism,"*Science* 240:1453–1459 (1988).

Rydén, M. et al., "ALK–7, a Novel Brain Specific Serine–Threonine Kinase Receptor," *Soc. Neutosci Abstr.* 21(1–3):1784, Abstract No. 703.7 (1995).

Shaw, D.R. et al., "Mouse/Human Chimeric Antibodies to a Tumor–Associated Antigen: Biologic Activity of the Four Human IgG Subclasses," *J. Natl. Cancer Inst.* 80(19):1553–1559 (1988).

Silver, P.A. et al., "Amino terminus of the yeast GAL4 gene product is sufficient for nuclear localization," *Proc. Natl. Acad. Sci. USA* 81:5951–5955 (1984).

Sun, L.K. et al., "Chimeric antibodies with human constant regions and mouse variable regions directed against carcinoma–associated antigen 17–1A, " *Proc. Natl. Acad. Sci. USA* 84:214–218 (1987).

Ten Dijke, P. et al., "Activin receptor–like kinases: a novel subclass of cell–surface receptors with predicted serine/threonine kinase activity," *Oncogene* 8:2879–2887 (1993).

Ten Dijke, P. et al., "Characterization of Type I Receptors for Transforming Growth Factor–β and Activin," *Science* 264:101–104 (1994).

Ulmanen, I. et al.,"Transcription and Translation of Foreign Genes in *Bacillus subtilis* by the Aid of a Secretion Vector," *J. Bacteriol.* 162(1):176–182 (1985).

Verhoeyen, M., "Reshaping Human Antibodies: Grafting an Antilysozyme Activity," *Science* 239:1534–1536 (1988).

Ward, J.M. et al.,"Construction and characterization of a series of multi–copy promoter–probe plasmid vectors for *Streptomyces* using the aminoglycoside phosphotransferase gene from Tn5 as indicator," *Mol. Gen. Genet.* 203:468–478 (1986).

Wood, C.R. et al., "The synthesis and in vivo assembly of functional antibodies in yeast," *Nature* 314:446–449 (1985).

5,789,565

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1482 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 1..1482

( x i ) SEQUENCE DESCRIPTION: SEQ ID NO:1:

```
ATG  ACC  CCA  GCA  AGC  CGC  TCC  GCA  CTG  AGC  CTG  GCC  CTC  CTG  CTG  GTG     48
Met  Thr  Pro  Ala  Ser  Arg  Ser  Ala  Leu  Ser  Leu  Ala  Leu  Leu  Leu  Val
 1                    5                       10                      15

GCA  CTG  GCC  TCC  GAC  CTT  GCG  GCA  GGA  CTG  AAG  TGT  GTG  TGT  CTT  TTG     96
Ala  Leu  Ala  Ser  Asp  Leu  Ala  Ala  Gly  Leu  Lys  Cys  Val  Cys  Leu  Leu
                     20                      25                      30
```

-continued

| | | | | | | | | | | | | | | | | |
|---|---|---|---|---|---|---|---|---|---|---|---|---|---|---|---|---|
| TGT | GAT | TCC | TCA | AAC | TTT | ACC | TGC | CAA | ACC | GAA | GGA | GCA | TGC | TGG | GCC | 144 |
| Cys | Asp | Ser 35 | Ser | Asn | Phe | Thr | Cys 40 | Gln | Thr | Glu | Gly | Ala 45 | Cys | Trp | Ala | |
| TCT | GTC | ATG | CTA | ACC | AAC | GGG | AAA | GAA | CAG | GTG | ATC | AAA | TCG | TGC | GTG | 192 |
| Ser | Val 50 | Met | Leu | Thr | Asn | Gly | Lys 55 | Glu | Gln | Val | Ile | Lys 60 | Ser | Cys | Val | |
| TCC | CTC | CCG | GAA | CTA | AAT | GCT | CAG | GTC | TTC | TGT | CAC | AGT | TCC | AAC | AAC | 240 |
| Ser | Leu 65 | Pro | Glu | Leu | Asn 70 | Ala | Gln | Val | Phe | Cys 75 | His | Ser | Ser | Asn | Asn 80 | |
| GTG | ACC | AAG | ACC | GAA | TGT | TGC | TTC | ACA | GAC | TTC | TGC | AAC | AAC | ATC | ACT | 288 |
| Val | Thr | Lys | Thr | Glu 85 | Cys | Cys | Phe | Thr | Asp 90 | Phe | Cys | Asn | Asn | Ile 95 | Thr | |
| CTG | CAC | CTT | CCC | ACA | GCA | TCT | CCA | GAT | GCC | CCT | AGA | CTT | GGC | CCC | ACA | 336 |
| Leu | His | Leu | Pro 100 | Thr | Ala | Ser | Pro | Asp 105 | Ala | Pro | Arg | Leu | Gly 110 | Pro | Thr | |
| GAG | CTG | ACA | GTT | GTT | ATC | ACT | GTA | CCT | GTT | TGC | CTC | CTG | TCC | ATC | GCA | 384 |
| Glu | Leu | Thr 115 | Val | Val | Ile | Thr | Val 120 | Pro | Val | Cys | Leu | Leu 125 | Ser | Ile | Ala | |
| GCC | ATG | CTA | ACG | ATA | TGG | GCC | TGC | CAG | GAC | CGC | CAG | TGC | ACA | TAC | AGG | 432 |
| Ala | Met | Leu | Thr 130 | Ile | Trp | Ala | Cys | Gln 135 | Asp | Arg | Gln | Cys | Thr 140 | Tyr | Arg | |
| AAG | ACC | AAG | AGA | CAC | AAT | GTG | GAG | GAA | CCA | CTG | GCA | GAG | TAC | AGC | CTT | 480 |
| Lys 145 | Thr | Lys | Arg | His | Asn 150 | Val | Glu | Glu | Pro | Leu 155 | Ala | Glu | Tyr | Ser | Leu 160 | |
| GTC | AAT | GCT | GGA | AAA | ACC | CTC | AAA | GAT | CTG | ATT | TAT | GAT | GCC | ACT | GCC | 528 |
| Val | Asn | Ala | Gly | Lys 165 | Thr | Leu | Lys | Asp | Leu 170 | Ile | Tyr | Asp | Ala | Thr 175 | Ala | |
| TCG | GGC | TCA | GGA | TCT | GGC | CTG | CCT | CTT | TTG | GTT | CAA | AGA | ACC | ATC | GCA | 576 |
| Ser | Gly | Ser | Gly 180 | Ser | Gly | Leu | Pro | Leu 185 | Leu | Val | Gln | Arg | Thr 190 | Ile | Ala | |
| AGG | ACA | ATT | GTA | CTT | CAA | GAA | ATC | GTA | GGA | AAA | GGT | CGG | TTT | GGG | GAA | 624 |
| Arg | Thr | Ile 195 | Val | Leu | Gln | Glu | Ile 200 | Val | Gly | Lys | Gly | Arg 205 | Phe | Gly | Glu | |
| GTG | TGG | CAC | GGA | AGA | TGG | TGT | GGA | GAA | GAT | GTG | GCT | GTG | AAA | ATA | TTC | 672 |
| Val | Trp 210 | His | Gly | Arg | Trp | Cys 215 | Gly | Glu | Asp | Val | Ala 220 | Val | Lys | Ile | Phe | |
| TCC | TCC | AGA | GAT | GAG | AGA | TCT | TGG | TTC | CGT | GAG | GCA | GAA | ATT | TAT | CAG | 720 |
| Ser 225 | Ser | Arg | Asp | Glu | Arg 230 | Ser | Trp | Phe | Arg | Glu 235 | Ala | Glu | Ile | Tyr | Gln 240 | |
| ACG | GTA | ATG | CTG | AGA | CAT | GAG | AAT | ATT | CTC | GGT | TTC | ATC | GCG | GCC | GAC | 768 |
| Thr | Val | Met | Leu | Arg 245 | His | Glu | Asn | Ile | Leu 250 | Gly | Phe | Ile | Ala | Ala 255 | Asp | |
| AAC | AAA | GAT | AAT | GGA | ACC | TGG | ACT | CAG | CTT | TGG | CTT | GTG | TCA | GAG | TAT | 816 |
| Asn | Lys | Asp | Asn | Gly 260 | Thr | Trp | Thr | Gln | Leu 265 | Trp | Leu | Val | Ser | Glu 270 | Tyr | |
| CAC | GAG | CAG | GGC | TCC | TTA | TAT | GAC | TAT | TTG | AAT | AGA | AAC | ATA | GTG | ACC | 864 |
| His | Glu | Gln | Gly 275 | Ser | Leu | Tyr | Asp | Tyr 280 | Leu | Asn | Arg | Asn | Ile 285 | Val | Thr | |
| GTG | GCT | GGA | ATG | GTC | AAG | TTG | GCG | CTT | TCA | ATA | GCG | AGT | GGT | CTG | GCT | 912 |
| Val | Ala | Gly 290 | Met | Val | Lys | Leu | Ala 295 | Leu | Ser | Ile | Ala | Ser 300 | Gly | Leu | Ala | |
| CAC | CTA | CAC | ATG | GAG | ATC | GTG | GGC | ACT | CAA | GGT | AAG | CCT | GCT | ATT | GCT | 960 |
| His | Leu | His 305 | Met | Glu | Ile | Val | Gly 310 | Thr | Gln | Gly | Lys | Pro 315 | Ala | Ile | Ala 320 | |
| CAC | CGA | GAT | ATA | AAG | TCA | AAG | AAT | ATC | TTA | GTC | AAA | AAG | TGT | GAC | ACT | 1008 |
| His | Arg | Asp | Ile | Lys 325 | Ser | Lys | Asn | Ile | Leu 330 | Val | Lys | Lys | Cys | Asp 335 | Thr | |
| TGT | GCC | ATA | GCT | GAC | TTA | GGG | CTG | GCT | GTG | AAA | CAT | GAT | TCT | ATC | ATG | 1056 |
| Cys | Ala | Ile | Ala 340 | Asp | Leu | Gly | Leu | Ala 345 | Val | Lys | His | Asp | Ser 350 | Ile | Met | |

| | | | | | | | | | | | | | | | | |
|---|---|---|---|---|---|---|---|---|---|---|---|---|---|---|---|---|
| AAC | ACT | ATA | GAT | ATA | CCC | CAG | AAT | CCT | AAA | GTG | GGA | ACC | AAG | AGG | TAT | 1104 |
| Asn | Thr | Ile 355 | Asp | Ile | Pro | Gln | Asn 360 | Pro | Lys | Val | Gly | Thr 365 | Lys | Arg | Tyr | |
| ATG | GCT | CCC | GAA | ATG | CTT | GAT | GAT | ACA | ATG | AAC | GTC | AAC | ATC | TTT | GAG | 1152 |
| Met | Ala 370 | Pro | Glu | Met | Leu | Asp | Asp 375 | Thr | Met | Asn | Val | Asn 380 | Ile | Phe | Glu | |
| TCC | TTC | AAG | CGA | GCT | GAC | ATC | TAT | TCG | GTG | GGG | CTG | GTT | TAC | TGG | GAA | 1200 |
| Ser 385 | Phe | Lys | Arg | Ala | Asp 390 | Ile | Tyr | Ser | Val | Gly 395 | Leu | Val | Tyr | Trp | Glu 400 | |
| ATA | GCT | CGA | AGG | TGT | TCA | GTT | GGA | GGA | CTT | GTT | GAA | GAG | TAC | CAG | TTG | 1248 |
| Ile | Ala | Arg | Arg | Cys 405 | Ser | Val | Gly | Gly | Leu 410 | Val | Glu | Glu | Tyr | Gln 415 | Leu | |
| CCT | TAT | TAT | GAC | ATG | GTG | CCT | TCA | GAT | CCT | TCC | ATA | GAG | GAA | ATG | AGG | 1296 |
| Pro | Tyr | Tyr | Asp 420 | Met | Val | Pro | Ser | Asp 425 | Pro | Ser | Ile | Glu | Glu 430 | Met | Arg | |
| AAG | GTC | GTT | TGT | GAT | CAG | AAA | CTC | CGA | CCA | AAT | CTC | CCA | AAC | CAG | TGG | 1344 |
| Lys | Val | Val 435 | Cys | Asp | Gln | Lys | Leu 440 | Arg | Pro | Asn | Leu | Pro 445 | Asn | Gln | Trp | |
| CAA | AGC | TGT | GAG | GCG | CTC | CGG | GTC | ATG | GGA | AGA | ATA | ATG | CGT | GAG | TGC | 1392 |
| Gln | Ser 450 | Cys | Glu | Ala | Leu | Arg 455 | Val | Met | Gly | Arg | Ile 460 | Met | Arg | Glu | Cys | |
| TGG | TAT | GCC | AAC | GGG | GCA | GCT | CGC | CTG | ACC | GCC | CTG | CGC | GTG | AAG | AAG | 1440 |
| Trp 465 | Tyr | Ala | Asn | Gly | Ala 470 | Ala | Arg | Leu | Thr | Ala 475 | Leu | Arg | Val | Lys | Lys 480 | |
| ACC | ATT | TCT | CAG | CTG | TGT | GTC | AAG | GAA | GAC | TGT | AAG | GCC | TAA | | | 1482 |
| Thr | Ile | Ser | Gln | Leu 485 | Cys | Val | Lys | Glu | Asp 490 | Cys | Lys | Ala | * | | | |

( 2 ) INFORMATION FOR SEQ ID NO:2:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Thr | Pro | Ala | Ser 5 | Arg | Ser | Ala | Leu | Ser 10 | Ala | Leu | Leu | Leu | Val 15 |
| Ala | Leu | Ala | Ser 20 | Asp | Leu | Ala | Ala | Gly 25 | Leu | Lys | Cys | Val | Cys 30 | Leu | Leu |
| Cys | Asp | Ser 35 | Ser | Asn | Phe | Thr | Cys 40 | Gln | Thr | Glu | Gly | Ala 45 | Cys | Trp | Ala |
| Ser | Val 50 | Met | Leu | Thr | Asn | Gly 55 | Lys | Glu | Gln | Val | Ile 60 | Lys | Ser | Cys | Val |
| Ser 65 | Leu | Pro | Glu | Leu | Asn 70 | Ala | Gln | Val | Phe | Cys 75 | His | Ser | Ser | Asn | Asn 80 |
| Val | Thr | Lys | Thr | Glu 85 | Cys | Cys | Phe | Thr | Asp 90 | Phe | Cys | Asn | Asn | Ile 95 | Thr |
| Leu | His | Leu | Pro 100 | Thr | Ala | Ser | Pro | Asp 105 | Ala | Pro | Arg | Leu | Gly 110 | Pro | Thr |
| Glu | Leu | Thr 115 | Val | Val | Ile | Thr | Val 120 | Pro | Val | Cys | Leu | Leu 125 | Ser | Ile | Ala |
| Ala | Met 130 | Leu | Thr | Ile | Trp | Ala 135 | Cys | Gln | Asp | Arg | Gln 140 | Cys | Thr | Tyr | Arg |
| Lys 145 | Thr | Lys | Arg | His | Asn 150 | Val | Glu | Glu | Pro | Leu 155 | Ala | Glu | Tyr | Ser | Leu 160 |
| Val | Asn | Ala | Gly | Lys 165 | Thr | Leu | Lys | Asp | Leu 170 | Ile | Tyr | Asp | Ala | Thr 175 | Ala |

| | | | | | | | | | | | | | | |
|---|---|---|---|---|---|---|---|---|---|---|---|---|---|---|
|Ser|Gly|Ser|Gly 180|Ser|Gly|Leu|Pro|Leu 185|Leu|Val|Gln|Arg|Thr 190|Ile|Ala|
|Arg|Thr|Ile 195|Val|Leu|Gln|Glu|Ile 200|Val|Gly|Lys|Gly|Arg 205|Phe|Gly|Glu|
|Val|Trp 210|His|Gly|Arg|Trp|Cys 215|Gly|Glu|Asp|Val|Ala 220|Val|Lys|Ile|Phe|
|Ser 225|Ser|Arg|Asp|Glu|Arg 230|Ser|Trp|Phe|Arg|Glu 235|Ala|Glu|Ile|Tyr|Gln 240|
|Thr|Val|Met|Leu|Arg 245|His|Glu|Asn|Ile|Leu 250|Gly|Phe|Ile|Ala|Ala 255|Asp|
|Asn|Lys|Asp|Asn 260|Gly|Thr|Trp|Thr|Gln 265|Leu|Trp|Leu|Val|Ser 270|Glu|Tyr|
|His|Glu|Gln 275|Gly|Ser|Leu|Tyr|Asp 280|Tyr|Leu|Asn|Arg|Asn 285|Ile|Val|Thr|
|Val|Ala 290|Gly|Met|Val|Lys|Leu 295|Ala|Leu|Ser|Ile|Ala 300|Ser|Gly|Leu|Ala|
|His 305|Leu|His|Met|Glu|Ile 310|Val|Gly|Thr|Gln|Gly 315|Lys|Pro|Ala|Ile|Ala 320|
|His|Arg|Asp|Ile|Lys 325|Ser|Lys|Asn|Ile|Leu 330|Val|Lys|Lys|Cys|Asp 335|Thr|
|Cys|Ala|Ile|Ala 340|Asp|Leu|Gly|Leu|Ala 345|Val|Lys|His|Asp|Ser 350|Ile|Met|
|Asn|Thr|Ile 355|Asp|Ile|Pro|Gln|Asn 360|Pro|Lys|Val|Gly|Thr 365|Lys|Arg|Tyr|
|Met|Ala|Pro 370|Glu|Met|Leu|Asp|Asp 375|Thr|Met|Asn|Val|Asn 380|Ile|Phe|Glu|
|Ser 385|Phe|Lys|Arg|Ala|Asp 390|Ile|Tyr|Ser|Val|Gly 395|Leu|Val|Tyr|Trp|Glu 400|
|Ile|Ala|Arg|Arg|Cys 405|Ser|Val|Gly|Gly|Leu 410|Val|Glu|Glu|Tyr|Gln 415|Leu|
|Pro|Tyr|Tyr|Asp 420|Met|Val|Pro|Ser|Asp 425|Pro|Ser|Ile|Glu|Glu 430|Met|Arg|
|Lys|Val|Val 435|Cys|Asp|Gln|Lys|Leu 440|Arg|Pro|Asn|Leu|Pro 445|Asn|Gln|Trp|
|Gln|Ser|Cys 450|Glu|Ala|Leu|Arg|Val 455|Met|Gly|Arg|Ile|Met 460|Arg|Glu|Cys|
|Trp|Tyr|Ala|Asn|Gly 470|Ala|Ala|Arg|Leu|Thr|Ala 475|Leu|Arg|Val|Lys|Lys 480|
|Thr|Ile|Ser|Gln|Leu 485|Cys|Val|Lys|Glu|Asp 490|Cys|Lys|Ala| | | |

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

GCGGATCCGT BGCHGTBAAR ATHTT      25

( 2 ) INFORMATION FOR SEQ ID NO:4:

( i ) SEQUENCE CHARACTERISTICS:
        ( A ) LENGTH: 6 amino acids
        ( B ) TYPE: amino acid (D) TOPOLOGY: unknown (xi) SEQUENCE DESCRIPTION: SEQ ID NO:4:

Val Ala Val Lys Ile Phe
1               5

(2) INFORMATION FOR SEQ ID NO:5:

(i) SEQUENCE CHARACTERISTICS:
    (A) LENGTH: 20 base pairs
    (B) TYPE: nucleic acid
    (C) STRANDEDNESS: unknown
    (D) TOPOLOGY: unknown (xi) SEQUENCE DESCRIPTION: SEQ ID NO:5:

CGGAATTCDG GDGCCATRTA                                                                20

(2) INFORMATION FOR SEQ ID NO:6:

(i) SEQUENCE CHARACTERISTICS:
    (A) LENGTH: 5 amino acids
    (B) TYPE: amino acid
    (D) TOPOLOGY: unknown (xi) SEQUENCE DESCRIPTION: SEQ ID NO:6:

Tyr Met Ala Pro Glu
1               5

1

SERINE THREONINE KINASE RECEPTOR, ALK-7

CROSS-REFERENCE TO RELATED APPLICATIONS

This application is a division of application Ser. No. 08/341,916, filed Nov. 15, 1994, now U.S. Pat. No. 5,614,609 which is a continuation-in-part of U.S. application Ser. No. 08/325,956, filed Oct. 20, 1994, (status:abandoned), the contents of which are incorporated herein by reference.

BACKGROUND OF THE INVENTION

1. Field of the Invention

The present invention relates, in general, to a novel serine threonine kinase receptor, ALK-7. In particular, the present invention relates to nucleic acid molecules coding for ALK-7; purified ALK-7 polypeptides; recombinant nucleic acid molecules; cells containing the recombinant nucleic acid molecules; antibodies having binding affinity specifically to ALK-7; hybridomas containing the antibodies; nucleic acid probes for the detection of ALK-7 nucleic acid; a method of detecting ALK-7 nucleic acids or polypeptides in a sample; and kits containing nucleic acid probes or antibodies. This invention further relates to bioassays using the nucleic acid sequence, receptor protein or antibodies of this invention to diagnose, assess, or prognose a mammal afflicted with neurodegenerative disease. Therapeutic uses for ALK-7 are also provided. This invention also relates to ligands, agonists, and antagonists of the ALK-7 receptor, and diagnostic and therapeutic uses thereof.

2. Background Information

Serine threonine kinase receptors are a family of growth factor signal transducers (He et al. (1993) *Dev. Dyn.* 196:133–142). A series of serine threonine kinase receptors, activin receptor-like kinases 1–6 (ALK-1 to -6), have been previously identified (ten Dijke et al. (1993) *Oncogene* 8:2879–2887; Franzen et al. (1993) *Cell* 75:681–692; Ebner et al. (1993) *Science* 260:1344; Matsuzaki et al. (1993) *J. Biol. Chem.* 268:12719; He et al. (1993) *Dev. Dyn.* 196:133–142; Attisano et al. (1993) *Cell* 75:681–692; ten Dijke et al. (1994) *Science* 264:101–104; WO 94/11502 published May 26, 1994). The present invention provides a novel serine threonine kinase receptor, ALK-7.

SUMMARY OF THE INVENTION

The invention provides an isolated nucleic acid molecule coding for a polypeptide comprising an amino acid sequence corresponding to a novel serine threonine kinase receptor, ALK-7.

The invention further provides a substantially pure polypeptide comprising an amino acid sequence corresponding to ALK-7.

The invention also provides a nucleic acid probe for the specific detection of the presence of ALK-7 in a sample.

The invention further provides a method of detecting ALK-7 nucleic acid in a sample.

The invention also provides a kit for detecting the presence of ALK-7 nucleic acid in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

2

The invention further provides a recombinant nucleic acid molecule comprising a sequence complimentary to an RNA sequence encoding an amino acid sequence corresponding to the above-described polypeptide.

The invention also provides a cell that contains the above-described recombinant nucleic acid molecule.

The invention further provides a non-human organism that contains the above-described recombinant nucleic acid molecule.

The invention also provides an antibody having binding affinity specifically to an ALK-7 polypeptide.

The invention further provides a method of detecting an ALK-7 polypeptide in a sample.

The invention also provides a method of measuring the amount of ALK-7 in a sample.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for human disease, in particular neurodegenerative diseases, disorders, and injuries.

The invention also provides methods for therapeutic uses involving all or part of the nucleic acid sequence encoding ALK-7 and its corresponding protein.

The invention provides assays for the isolation of ligands, agonists and antagonists of the ALK-7 receptor and therapeutic uses for these molecules.

The invention also provides assays for the assessment and development of drugs capable of activating or suppressing the ALK-7 receptor and therapeutic uses for these drugs.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into MRNA that is then translated into a sequence of amino acids characteristic of a specific polypeptide.

Restiction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome can be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Substantially Pure. A "substantially pure" protein or nucleic acid is a protein or nucleic acid preparation that is generally lacking in other cellular components.

Ligand. Ligand refers to any protein or proteins that can interact with the ALK-7 receptor binding domain. The ligand or ligands can be soluble or membrane bound. The ligand or ligands can be a naturally occurring protein, or synthetically or recombinantly produced. The ligand can also be a nonprotein molecule that acts as ligand when it interacts with the ALK-7 receptor binding domain. Interactions between the ligand and receptor binding domain include, but are not limited to, any covalent or non-covalent interactions. The receptor binding domain is any region of the ALK-7 receptor molecule that interacts directly or indirectly with the ALK-7 ligand. Agonists and antagonists of ALK-7 that can interact with the ALK-7 receptor binding domain are ligands.

Neurodegenerative disease. The term neurodegenerative disease includes, but is not limited to, states in a mammal which can include chromosomal abnormalities, degenerative growth and developmental disorders, viral infections, bacterial infections, brain injuries, or neoplastic conditions. Examples of neurodegenerative diseases that can be diagnosed, assessed or treated by methods described in the present application include, but are not limited to, Alzheimer's disease, epilepsy, schizophrenia. In a preferred embodiment diseases characterized by neurodegeneration in the limbic system are diagnosed, assessed or treated by methods disclosed in the present application. Examples of injuries to the nervous system include, but are not limited to, stroke and cerebral ischemia due to stroke or cardiac arrest. Also considered within this definition is the treatment of injury to the nervous system. Further, neoplasms involving neuronal tissue can be diagnosed, assessed or therapeutically treated by methods suggested herein.

Drug. Drugs include, but are not limited to proteins, peptides, degenerate peptides, agents purified form conditioned cell medium, organic molecules, inorganic molecules, antibodies or oligonucleotides. Other candidate drugs include analogs of the ALK-7 ligand or ligands. The drug can be naturally occurring or synthetically or recombinantly produced. One skilled in the art will understand that such drugs can be developed by the assays described below.

DETAILED DESCRIPTION OF THE INVENTION

For purposes of clarity of disclosure, and not by way of limitation, the detailed description of the invention is divided into the following subsections:

I. Isolated Nucleic Acid Molecules Coding for ALK-7 Polypeptides.
II. Substantially Pure ALK-7 Polypeptides.
III. A Nucleic Acid Probe for the Specific Detection of ALK-7.
IV. A Method of Detecting The Presence of ALK-7 in a Sample.
V. A Kit for Detecting the Presence of ALK-7 in a Sample.
VI. DNA Constructs Comprising an ALK-7 Nucleic Acid Molecule and Cells Containing These Constructs.
VII. An Antibody Having Binding Affinity to an ALK-7 Polypeptide and a Hybridoma Containing the Antibody.
VIII. A Method of Detecting an ALK-7 Polypeptide in a Sample.
IX. A Diagnostic Kit Comprising Antibodies to ALK-7.
X. Diagnostic Screening and Treatment I. Isolated Nucleic Acid Molecules Coding for ALK-7 Polypeptides In one embodiment, the present invention relates to an isolated nucleic acid molecule coding for a polypeptide having an amino acid sequence corresponding to a novel serine threonine kinase receptor, ALK-7. In one preferred embodiment, the isolated nucleic acid molecule comprises an ALK-7 nucleotide sequence with greater than 70% similarity to the ALK-7 nucleotide sequence present in SEQ ID NO:1 (preferably greater than 80%; more preferably greater than 90%). In another preferred embodiment, the isolated nucleic acid molecule comprises the ALK-7 nucleotide sequence present in SEQ ID NO:1. In another embodiment, the isolated nucleic acid molecule encodes the ALK-7 amino acid sequence present in SEQ ID NO:2.

Also included within the scope of this invention are the functional equivalents of the herein-described isolated nucleic acid molecules and derivatives thereof. For example, the nucleic acid sequences depicted in SEQ ID NO:1 can be altered by substitutions, additions or deletions that provide for functionally equivalent molecules. Due to the degeneracy of nucleotide coding sequences, other DNA sequences which encode substantially the same amino acid sequence as depicted in SEQ ID NO:2 can be used in the practice of the present invention. These include but are not limited to nucleotide sequences comprising all or portions of ALK-7 nucleic acid depicted in SEQ ID NO:1 which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the ALK-7 gene and fragments thereof permitted by the genetic code are, therefore, included in this invention.

In addition, the nucleic acid sequence can comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide can be used in this regard, provided that its addition, deletion or substitution does not alter the amino acid sequence of SEQ ID NO:2 which is encoded by the nucleotide sequence. Moreover, the nucleic acid molecule of the present invention can, as necessary, have restriction endonuclease recognition sites added to its 5'-end and/or 3'-end.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to ALK-7 are provided. In particular, the nucleic acid molecule can be isolated from a biological sample containing human RNA or DNA.

The nucleic acid molecule can be isolated from a biological sample containing human RNA using the techniques of cDNA cloning and subtractive hybridization. The nucleic acid molecule can also be isolated from a cDNA library using a homologous probe.

The nucleic acid molecule can be isolated from a biological sample containing human genomnic DNA or from a genomic library. Suitable biological samples include, but are not limited to, blood, semen and tissue. The method of obtaining the biological sample will vary depending upon the nature of the sample.

One skilled in the art will realize that the human genome can be subject to slight allelic variations between individuals. Therefore, the isolated nucleic acid molecule is also intended to include allelic variations, so long as the sequence is a functional derivative of the ALK-7 gene. When an ALK-7 allele does not encode the identical sequence to that found in SEQ ID NO:1, it can be isolated and identified as ALK-7 using the same techniques used herein, and especially PCR techniques to amplify the appropriate gene with primers based on the sequences disclosed herein.

One skilled in the art will realize that organisms other than rats will also contain ALK-7 genes (for example, eukaryotes; more specifically, mammals, birds, fish, and plants; more specifically, humans, gorillas, rhesus monkeys, and chimpanzees; preferably, human ALK-7). The invention is intended to include, but not be limited to, ALK-7 nucleic acid molecules isolated from the above-described organisms.

B. Synthesis of Nucleic Acid

Isolated nucleic acid molecules of the present invention are also meant to include those chemically synthesized. For example, a nucleic acid molecule with the nucleotide sequence which codes for the expression product of an ALK-7 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185–3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

II. Substantially Pure ALK-7 Polypeptides

In another embodiment, the present invention relates to a substantially pure polypeptide having an amino acid sequence corresponding to ALK-7, or a functional derivative thereof. In a preferred embodiment, the polypeptide has the amino acid sequence set forth in SEQ ID NO:2, or mutant or species variation thereof, or at least 70% identity or at least 85% similarity thereof (preferably, at least 90% identity or at least 95% similarity thereof), or at least 43 contiguous amino acids thereof (preferably, at least 50 or 100 contiguous amino acids thereof).

Amino acid sequence variants of ALK-7 can be prepared by mutations in the DNA. Such variants include, for example, deletions from, or insertions or substitutions of, residues within the amino acid sequence shown in SEQ ID NO:2. Any combination of deletion, insertion, and substitution can also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure.

While the site for introducing an amino acid sequence variation is predetermined, the mutation per se need not be predetermined. For example, to optimize the performance of a mutation at a given site, random mutagenesis can be conducted at the target codon or region and the expressed ALK-7 variants screened for the optimal combination of desired activity. Techniques for making substitution mutations at predetermined sites in DNA having a known sequence are well known, for example, site-specific mutagenesis.

Preparation of an ALK-7 variant in accordance herewith is preferably achieved by site-specific mutagenesis of DNA that encodes an earlier prepared variant or a nonvariant version of the protein. Site-specific mutagenesis allows the production of ALK-7 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete ALK-7 sequence) can range generally from about 1 to 10 residues, more preferably 1 to 5.

The third group of variants are those in which at least one amino acid residue in the ALK-7 molecule, and preferably, only one, has been removed and a different residue inserted in its place. Such substitutions preferably are made in accordance with the following Table 1 when it is desired to modulate finely the characteristics of ALK-7.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |

TABLE 1-continued

| Original Residue | Exemplary Substitutions |
|---|---|
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of ALK-7. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native ALK-7 encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified ALK-7 molecule variant is then screened in a suitable screening assay for the desired characteristic. For example, a change in the immunological character of the ALK-7 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments could be used to expressed the ALK-7 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromoto-graphy, size-exclusion chromatography, HPLC, ion-exchange chromato-graphy, and immuno-affinity chromatography.

III. A Nucleic Acid Probe for the Specific Detection of ALK-7

In another embodiment, the present invention relates to a nucleic acid probe for the specific detection of the presence of ALK-7 in a sample comprising the above-described nucleic acid molecules or at least a fragment thereof which binds under stringent conditions to ALK-7 but not ALK-1 through ALK-6. The probe is designed such that it does not have 100% homology with a similarly located ALK probe.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual, second edition*, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the ALK-7. Thus, the synthesized nucleic acid probes can be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual, second edition*, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of ALK-7 in a Sample

In another embodiment, the present invention relates to a method of detecting the presence of ALK-7 in a sample comprising a) contacting the sample with the above-described nucleic acid probe, under conditions such that hybridization occurs, and b) detecting the presence of the probe bound to the nucleic acid molecule. One skilled in the art would select the nucleic acid probe according to techniques known in the art as described above. Samples to be tested include but should not be limited to RNA samples of human tissue.

ALK-7 has been found to be expressed in brain cells. Accordingly, ALK-7 probes can be used detect the presence of RNA from brain cells in a sample. Further, altered expression levels of ALK-7 RNA in an individual, as compared to normal levels, can indicate the presence of disease. The ALK-7 probes can further be used to assay cellular activity in general and specifically in brain tissue.

V. A Kit for Detecting the Presence of ALK-7 in a Sample

In another embodiment, the present invention relates to a kit for detecting the presence of ALK-7 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising an ALK-7Nucleic Acid Molecule and Cells Containing These Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an ALK-7 gene can be obtained by the above-described methods. This region can be retained for its transcriptional termination regulatory sequences, such as termination and polyadenylation. Thus, by retaining the 3'-region naturally contiguous to the DNA sequence encoding an ALK-7 gene, the transcriptional termination signals can be provided. Where the transcriptional termination signals are not satisfactorily functional in the expression host cell, then a 3' region functional in the host cell can be substituted.

Two DNA sequences (such as a promoter region sequence and an ALK-7 sequence) are said to be operably linked if the nature of the linkage between the two DNA sequences does not (1) result in the introduction of a frame-shift mutation, (2) interfere with the ability of the promoter region sequence to direct the transcription of an ALK-7 gene sequence, or (3) interfere with the ability of the ALK-7 gene sequence to be transcribed by the promoter region sequence. Thus, a promoter region would be operably linked to a DNA sequence if the promoter were capable of effecting transcription of that DNA sequence.

The present invention encompasses the expression of the ALK-7 gene (or a functional derivative thereof) in either prokaryotic or eukaryotic cells. Prokaryotic hosts are, generally, the most efficient and convenient for the production of recombinant proteins and, therefore, are preferred for the expression of the ALK-7 gene.

Prokaryotes most frequently are represented by various strains of E. coli. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as E. coli, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express ALK-7 in a prokaryotic cell, it is necessary to operably link the ALK-7 sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of E. coli, the α-amylase (Ulmanen et al., J. Bacteriol. 162:176–182 (1985)) and the ζ-28-specific promoters of B. subtilis (Gilman et al., Gene sequence 32:11–20 (1984)), the promoters of the bacteriophages of Bacillus (Gryczan, In: The Molecular Biology of the Bacilli, Academic Press, Inc., New York (1982)), and Streptomyces promoters (Ward et al., Mol. Gen. Genet. 203:468–478 (1986)). Prokaryotic promoters are reviewed by Glick (J. Ind. Microbiol. 1:277–282 (1987)); Cenatiempo (Biochimie 68:505–516 (1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et al. (Ann. Rev. Microbio 35:365–404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of the ALK-7 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of ALK-7 in insects cells (Jasny, *Science* 238:1653 (1987); Miller et al., In: *Genetic Engineering* (1986), Setlow, J. K., et al., eds., Plenum, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous ALK-7 protein. Furthermore, different vector/host expression systems can effect processing reactions such as proteolytic cleavages to different extents.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of ALK-7.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of ALK-7 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer .et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (USA) 79:6971–6975 (1982); Silver et al., *Proc. Natl. Acad. Sci.* (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes ALK-7 does not contain any intervening codons which are capable of encoding a methionine (i.e., AUG). The presence of such codons results either in a formation of a fusion protein (if the AUG codon is in the same reading frame as the ALK-7 coding sequence) or a frame-shift mutation (if the AUG codon is not in the same reading frame as the ALK-7 coding sequence).

An ALK-7 nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)).

Once the vector or nucleic acid molecule containing the DNA construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of ALK-7. This can take place in the transformed cells as such, or following the induction of these cells to differentiate (for example, by administration of bromodeoxyuracil to neuroblastoma cells or the like).

VII. An Antibody Having Binding Affinity to an ALK-7Polypeptide and a Hybridoma Containing the Antibody In another embodiment, the present invention relates to an antibody having binding affinity specifically to an ALK-7 polypeptide as described above or specifically to an ALK-7 polypeptide binding fragment thereof. An antibody binds specifically to an ALK-7 polpeptide or binding fragment thereof if it does not bind to ALK-1 to ALK-6. Those which bind selectively to ALK-7 would be chosen for use in methods which could include, but should not be limited to, the analysis of altered ALK-7 expression in tissue containing ALK-7.

The ALK-7 proteins of the present invention can be used in a variety of procedures and methods, such as for the generation of antibodies, for use in identifying pharmaceutical compositions, and for studying DNA/protein interaction.

The ALK-7 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to ALK-7 which are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1,043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth.*

*Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*"4th Ed., Blackwell Scientific Publications, Oxford, England, Chapter 10 (1986); Jacoby et al., *Meth. Enzym.* 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, N.Y., pp. 289-307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the ALK-7 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting an ALK-7 Polypeptide in a Sample

In another embodiment, the present invention relates to a method of detecting an ALK-7 polypeptide in a sample, comprising: a) contacting the sample with an above-described antibody, under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of ALK-7 in a sample as compared to normal levels can indicate a specific disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising Antibodies to ALK-7

In another embodiment of the present invention, a kit is provided which contains all the necessary reagents to carry out the previously described methods of detection. The kit can comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening and Treatment

It is to be understood that although the following discussion is specifically directed to human patients, the teachings are also applicable to any animal that expresses ALK-7.

The diagnostic and screening methods of the invention are especially useful for a patient suspected of being at risk for developing a disease associated with an altered expression level of ALK-7 based on family history, or a patient in which it is desired to diagnose an ALK-7-related disease.

According to the invention, presymptomatic screening of an individual in need of such screening is now possible using DNA encoding the ALK-7 protein of the invention. The screening method of the invention allows a presymptomatic diagnosis, including prenatal diagnosis, of the presence of a missing or aberrant ALK-7 gene in individuals; and thus an opinion concerning the likelihood that such individual would develop or has developed an ALK-7-associated disease. This is especially valuable for the identification of carriers of altered or missing ALK-7 genes, for example, from individuals with a family history of an ALK-7-associated disease. Early diagnosis is also desired to maximize appropriate timely intervention.

In one preferred embodiment of the method of screening, a tissue sample would be taken from such individual, and screened for (1) the presence of the "normal" ALK-7 gene; (2) the presence of ALK-7 mRNA and/or (3) the presence of ALK-7 protein. The normal human gene can be characterized based upon, for example, detection of restriction digestion patterns in "normal" versus the patient's DNA, including RFLP analysis, using DNA probes prepared against the ALK-7 sequence (or a functional fragment thereof) taught in the invention. Similarly, ALK-7 mRNA can be characterized and compared to normal ALK-7 mRNA (a) levels and/or (b) size as found in a human population not at risk of developing ALK-7-associated disease using similar probes. Lastly, ALK-7 protein can be (a) detected and/or (b) quantitated using a biological assay for ALK-7 activity or using an immunological assay and ALK-7 antibodies. When assaying ALK-7 protein, the immunological assay is preferred for its speed. An (1) aberrant ALK-7 DNA size pattern, and/or (2) aberrant ALK-7 mRNA sizes or levels and/or (3) aberrant ALK-7 protein levels would indicate that the patient is at risk for developing an ALK-7-associated disease.

The screening and diagnostic methods of the invention do not require that the entire ALK-7 DNA coding sequence be used for the probe. Rather, it is only necessary to use a fragment or length of nucleic acid that is sufficient to detect the presence of the ALK-7 gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal ALK-7 gene is present in a heterozygous state.

In the method of treating an ALK-7-associated disease in a patient in need of such treatment, functional ALK-7 DNA can be provided to the cells of such patient in a manner and amount that permits the expression of the ALK-7 protein provided by such gene, for a time and in a quantity sufficient to treat such patient. Many vector systems are known in the art to provide such delivery to human patients in need of a gene or protein missing from the cell. For example, retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441. Delivery of a DNA sequence encoding a functional ALK-7 protein will effectively replace the missing or mutated ALK-7 gene of the invention.

In an alternative embodiment stem cell populations for either neuronal or glial cells can be genetically engineered to express a functional ALK-7 receptor. Such cells recombinantly expressing the ALK-7 receptor, can be transplanted to the diseased or injured region of the mammal's neurological system (*Neural Transplantation. A Practical Approach*, Donnet & Djorklund, eds., Oxford University Press, New York, N.Y. (1992)). In yet another alternative embodiment, embryonic tissue or fetal neurons can be genetically engineered to express functional ALK-7 receptor and transplanted to the diseased or injured region of the mammal's limibic system. The feasibility of transplanting fetal dopamine neurons into Parkinsonian patients has been demonstrated. (Lindvall et al., *Archives of Neurology* 46:615–631 (1989)).

Studies of the molecular interactions between ligands and their receptors showed that only the extracellular domain of the receptor is involved in the special physical interaction between the molecules (Riedel et al., *Nature* 324:68–70 (1986); Riedel et al *EMBO J.* 8:2943–2945 (1989)). Thus, the extracellular domain of a receptor can be used as a probe to screen an expression cDNA library for the ALK-7 ligand or ligands. In one approach for detection of the receptor probe, placental alkaline phosphatase will be fused to the extracellular domain of a receptor, and positive clones will be detected by the presence of alkaline phosphatase activity.

An alternative approach to isolate the ALK-7 ligand is to utilize the findings that co-expression of a receptor and its ligand in the same cells results in uncontrolled proliferation and malignant transformation (Klein et al., *Cell* 66:395–403 (1991); Gazit et al., *Cell* 39:89–97 (1984)). A eukaryotic cDNA expression library can be transfected into cells expressing a receptor, and the presence of a ligand will create an autocrine loop, resulting in a transformed phenotype. This approach has been successfully used by Miki et al., *Science* 251:72–75 (1991), to isolate the receptor of the keratinocyte growth factor (KGF) using cells expressing KGF. In yet another alternative approach the ALK-7 receptor protein can be expressed in a cell line or in Xenopus oocytes by the recombinant techniques described above and its ligand stimulated activation of tyrosine kinase activity, as detected by an anti-phosphotryosine antibody (UBI, Happauge, N.Y.) can be used to assay and purify the ligand. For example, cells expressing the recombinant ALK-7 receptor can be exposed to mammalian brain extract. The brain extracts can be fractionated by chromatography and used to assay for the presence of the ligand activity. Once an activity is identified in a particular fraction, it can be further purified by conventional biochemical techniques.

In another alternative approach, the ALK-7 extracellular domain can be used to screen a random peptide library (Cull et al., *Proc. Natl. Acad. Sci. USA* 89:1865–1869 (1982); Lam et al., *Nature* 354:82–84 (1991)). Peptides isolated can be assayed for their ligand activity.

In another embodiment of this invention, the ALK-7 ligand is expressed as a recombinant gene in a cell, so that the cells can be transplanted into a mammal, preferably a human in need of gene therapy. To provide gene therapy to an individual, a genetic sequence which encodes for all or part of the ALK-7 ligand is inserted into a vector and introduced into a host cell. Examples of diseases that can be suitable for gene therapy include, but are not limited to, neurodegenerative diseases or disorders, Alzheimer's, schizophrenia, epilepsy, neoplasms and cancer. Examples of vectors that may be used in gene therapy include, but are not limited to, defective retroviral, adenoviral, or other viral vectors (Mulligan, R. C., *Science* 260:926–932 (1993)). The means by which the vector carrying the gene can be introduced into the cell include but is not limited to, microinjection, electroporation, transduction, or transfection using DEAE-Dextran, lipofection, calcium phosphate or other procedures known to one skilled in the art (*Molecular Cloning, A Laboratory Manual*, Sambrook et al., eds., Cold Spring Harbor Press, Plainview, N.Y. (1989)).

The ability of antagonists and agonists of ALK-7 to interfere or enhance the activity of ALK-7 can be evaluated with cells containing ALK-7. An assay for ALK-7 activity in cells can be used to determine the functionality of the ALK-7 protein in the presence of an agent which may act as antagonist or agonist, and thus, agents that interfere or enhance the activity of ALK-7 are identified.

The agents screened in the assays can be, but are not limited to, peptides, carbohydrates, vitamin derivatives, or other pharmaceutical agents. These agents can be selected and screened 1) at random, 2) by a rational selection or 3) by design using for example, protein or ligand modeling techniques.

For random screening, agents such as peptides, carbohydrates, pharmaceutical agents and the like are selected at random and are assayed for their ability to bind to or stimulate/block the activity of ALK-7 protein.

Alternatively, agents may be rationally selected or designed. As used herein, an agent is said to be "rationally selected or designed" when the agent is chosen based on the configuration of the ALK-7 protein or known ligand.

In one embodiment, the present invention relates to a method of screening for an antagonist or agonist which stimulates or blocks the activity of ALK-7 comprising:

(a) incubating a cell expressing ALK-7 with an agent to be tested; and (b) assaying the cell for the activity of the ALK-7 protein by measuring the agents effect on ALK-7 binding of ALK-7 ligand.

Any cell may be used in the above assay so long as it expresses a functional form of ALK-7 protein and the ALK-7 activity can be measured. The preferred expression cells are eukaryotic cells or organisms. Such cells can be modified to contain DNA sequences encoding the ALK-7 protein using routine procedures known in the art. Alternatively, one skilled in the art can introduce mRNA encoding the ALK-7 protein directly into the cell.

Using ALK-7 ligands (including antagonists and agonists as described above) the present invention further provides a method for modulating the activity of the ALK-7 protein in a cell. In general, agents (antagonists and agonists) which have been identified to block or stimulate the activity of ALK-7 can be formulated so that the agent can be contacted with a cell expressing an ALK-7 protein in vivo. The contacting of such a cell with such an agent results in the in vivo modulation of the activity of the ALK-7 proteins. So long as a formulation barrier or toxicity barrier does not exist, agents identified in the assays described above will be effective for in vivo use.

In another embodiment, the present invention relates to a method of administering ALK-7 or an ALK-7 ligand (including ALK-7 antagonists and agonists) to an animal (preferably, a mammal (specifically, a human)) in an amount sufficient to effect an altered level of ALK-7 in the animal. The administered ALK-7 or ALK-7 ligand could specifically effect ALK-7 associated functions. Further, since ALK-7 is expressed in brain tissue, administration of ALK-7 or ALK-7 ligand could be used to alter ALK-7 levels in the brain.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of ALK-7 or ALK-7 ligand, in one or more administrations daily, for one or several days. ALK-7 or ALK-7 ligand can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, *Remington's Pharmaceutical Science*, 16th Ed., Mack Eds. (1980).

In another embodiment, the present invention relates to a pharmaceutical composition comprising ALK-7 or ALK-7 ligand in an amount sufficient to alter ALK-7 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton Pa. (1980) and WO 91/19008).

The present invention is described in further detail in the following non-limiting examples.

EXAMPLE 1

Isolation of ALK-7

A PCR fragment of ALK-7 was isolated using primer 5'-GCGGATCCGT(C/G/T)CG(A/C/T)GT(C/G/T)AA(A/G)AT(A/C/T)TT-3' (SEQ ID NO:3), derived from the motif VAVKIF (SEQ ID NO:4) with a BamHI restriction site and primer 5'-CGGAATTC(A/G/T)GG(A/G/T) GCCAT(A/G) TA-3'(SEQ ID NO:5), derived from the motif YMAPE (SEQ ID NO:6) with an EcoRI restriction site. PCR amplification was done for five cycles, each composed of 94° C. (1 min), 50° C. (1 min) and 72° C. (1 min), followed by 35 cycles, each composed of 940° C. (1 min), 55° C. (1 min) and 72° C. (1 min).

This PCR fragment was used to clone a full-length cDNA from a λgt10 postnatal day 7 total rat-brain library, washing at high stringency (60° C. 0.1% SDS, 0.1 XSSC) (for general techniques, See, *Molecular Cloning: A Laboratory Manual, second edition*, edited by Sambrook, Fritsch, & Maniatis, Cold Spring Harbor Laboratory, 1989). The full length ALK-7 cDNA clone was deposited with the American Type Culture Collection, 12301 Parklawn Drive, Rockville, Md. 20852 and was given the accession number ATCC 75945. The nucleotide and amino acid sequences of the coding region of the ALK-7 clone is presented in SEQ ID NOS:1 and 2, respectively.

EXAMPLE 2

Isolation of an ALK-7 Ligand

Screening of a cDNA Expression Library For ALK-7 Ligand Using an Extracellular Domain-Alkaline Phosphatase Fusion Protein As a Probe To construct a fusion protein between the extracellular domain of ALK-7 and the secreted placental alkaline phosphatase (SEAP), a vector named APtag-1, constructed by Flannagan & Leder, *Cell* 63:185–194 (1990), is used. APtag-1 contains a set of restriction sites for the insertion of the region of the ALK-7 cDNA encoding the extracellular domain. Downstream of the insertion sites is the full length sequence of SEAP, which is fused to the upstream sequence.

To generate an ALK-7 receptor fusion protein, the 5' end of the ALK-7 cDNA sequence is inserted into APtag-1, including sequences encoding the ALK-7 secretion signal peptide and the entire extracellular domain, ending immediately before the first hydrophobic amino acid of the transmembrane region. The resulting plasmid encodes a fusion protein with the ALK-7 extracellular domain joined to a SEAP. The fusion protein is expressed from a Moloney Murine Leukemia virus LTR promoter. The fusion construct is transfected into NIH/3T3 cells which have been shown to express high levels of an APtag-Kit fusion protein (Flannagan & Leder, *Cell* 63:185–194 (1990)). The fusion construct is contransfected with a selectable marker plasmid pSV2neo, and selected with G418 (400–800 µg/ml). Neo-resistant colonies are grown in 96-well plates and screened for secretion of SEAP activity into the media. The fusion protein is concentrated, purified and used as a probe to screen a cDNA expression library from mammalian brain, preferably human.

Three types of positive clones are expected: (1) clones having background alkaline phosphatase activity; (2) clones which bind non-specifically to the fusion protein; and (3) clones encoding the ALK-7 ligand. Background phosphatase clones will be positive without the added probe in the presence of alkaline phosphatase substrates. To distinguish the specific from the non-specific interacting clones, extracts from bacteria expressing these clones are used to stimulate the kinase activity of ALK-7 in ALK-7 expressing NIH/3T3 cells. Only the ligand will be able to stimulate activation of ALK-7 kinase activity.

It is preferable to produce the receptor probe in NIH/3T3 cells rather than bacteria to receive proper glycosylation of the ALK-7 extracellular domain. It has however been demonstrated that glycosylation of growth factors is often not necessary for their activity. For example, M-CSF (Metcalf, *Blood* 67:257–267 (1986) and NGF (available from Boehringer Mannheim) produced in bacteria are biologically active. Therefore, the glycosylated receptor probe should interact properly with its ligand synthesized by *E. coli* in a phase plaque during the screening.

In addition to using the Ap-tagged ALK-7 probe to screen for ALK-7 ligand in vitro, the probe can also be used in histological staining on mammalian brain section to localize expression of the ligand. Determination of the loci of expression of the ALK-7 ligand will allow for biochemical purification of the ligand from that tissue cell source further for analysis.

Functional Screening of the ALK-7 Ligand

An alternative approach to isolate the ALK-7 ligand is to utilize a functional screening approach. Full length cDNA of ALK-7 is cloned into an expression vector pMEX under a MMLV LTR promoter. The ALK-7 expression vector is co-transfected into NIH/3T3 cells together with pSV2Hygro containing a hygromycin β-phosphotransferase gene which confers hygromycin resistance (Gritz & Davies, *Gene* 25:179–188 (1983)). The transfected cells are selected with hygromycin B at a concentration of 350µg/ml. The resistant clones are grown in 12-well plates and screened for ALK-7 expression with anti-ALK-7 antibody by Western blot analysis.

The vector system developed by Miki et al., *Gene* 83:137–146 (1989) is used to construct a directional eukaryotic cDNA library from rat brain mRNA. The vector has a MMLV LTR promoter for the expression of cDNA inserts and a SV40 early promoter-driven Neo gene as a selectable marker. In addition, this vector contains a pBR322 replication origin, and the cDNA inserts of interest can be obtained easily by Not I digestion of crude Lambda DNA preparations and ligation followed by transfection of bacterial cells. The cDNA library is constructed as described in detail by Miki et al., *Gene* 83:137–146 (1989).

The cDNA library is transfected into ALK-7-expressing NIH/3T3 mouse embryo fibroblasts. Foci from transfected cells are isolated and tested for Neo resistance to eliminate the background transformation in NIH/3T3 cells. Genomic DNA from each Neo-resistant transformant is cleaved by Not I which releases the plasmid. Digested DNA is ligated under diluted conditions and used to transform competent bacteria. Plasmid DNA from each focus is purified and transfected in NIH/3T3 cells with or without ALK-7 expression. The transformation by the ALK-7 ligand but not other proteins is expected to be dependent on the presence of ALK-7 expression. Clones are then further analyzed by sequencing, the encoded protein purified and assayed for ALK-7 binding.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. An isolated nucleic acid molecule wherein the molecule encodes the amino acid sequence set forth in SEQ ID NO:2.

2. The isolated nucleic acid molecule according to claim 1, wherein the molecule has the nucleic acid sequence set forth in SEQ ID NO:1.

3. A recombinant nucleic acid molecule comprising, 5' to 3', a promoter effective to initiate transcription in a host cell and the isolated nucleic acid molecule according to claim 1.

4. A recombinant nucleic acid molecule comprising a vector and the isolated nucleic acid molecule according to claim 1.

5. A cell that contains the recombinant nucleic acid molecule according to any one of claims 3 or 4.

* * * * *